United States Patent
Brucker et al.

(10) Patent No.: US 6,425,894 B1
(45) Date of Patent: Jul. 30, 2002

(54) ABLATION CATHETER WITH ELECTRODE TEMPERATURE MONITORING

(75) Inventors: Gregory Brucker, Minneapolis; William Penny, Arden Hill, both of MN (US)

(73) Assignee: BioSense Webster, Inc., Diamond Bar, CA (US)

( * ) Notice: Subject to any disclaimer, the term of this patent is extended or adjusted under 35 U.S.C. 154(b) by 9 days.

(21) Appl. No.: 09/614,362

(22) Filed: Jul. 12, 2000

(51) Int. Cl.[7] .............................................. A61B 18/18
(52) U.S. Cl. ........................... 606/41; 607/101; 607/102
(58) Field of Search .............................. 606/31, 41, 42; 607/101, 102; 600/549

(56) References Cited

U.S. PATENT DOCUMENTS

| | | | |
|---|---|---|---|
| 4,411,266 A | * 10/1983 | Cosman | 600/549 |
| 5,293,877 A | * 3/1994 | O'Hara et al. | 374/131 |
| 5,931,835 A | * 8/1999 | Mackey | 606/34 |
| 5,957,961 A | * 9/1999 | Maguire et al. | 600/549 |
| 6,050,994 A | * 4/2000 | Sherman | 606/42 |
| 6,162,184 A | * 12/2000 | Swanson et al. | 600/549 |
| 6,245,065 B1 | * 6/2001 | Panescu et al. | 606/40 |

* cited by examiner

Primary Examiner—Linda C. M. Dvorak
Assistant Examiner—Kenneth G Schopfer
(74) Attorney, Agent, or Firm—George H. Gerstman; Seyfarth Shaw

(57) ABSTRACT

An ablation catheter is provided which comprises an elongated catheter body, a plurality of electrodes, and a thermal monitoring circuit. The thermal monitoring circuit is comprised of a plurality of thermocouples joined in series. The thermocouples thermoconductively coupled to the electrodes. The thermal monitoring circuit will require only two wires to travel through the elongated catheter body in order to monitor a plurality of electrodes.

20 Claims, 1 Drawing Sheet

ABLATION CATHETER WITH ELECTRODE TEMPERATURE MONITORING

FIELD OF THE INVENTION

The present invention concerns catheters used for the treatment of cardiac arrhythmias. More specifically, the present invention relates to a novel ablation catheter having an electrode temperature monitoring system.

BACKGROUND OF THE INVENTION

Cardiac arrhythmias are often caused when portions of the heart form alternative conduction pathways which transmit electrical signals that interfere with the normal conduction of electrical signals which regulate the beating of the heart. In order to treat cardiac arrhythmias stemming from this problem, the cells which comprise these alternative conduction pathways must either be destroyed or the conductive pathways from these cells be blocked from transmitting electrical signals to the rest of the heart.

One way to treat this ailment is through the use of a procedure called Radio Frequency Ablation (RFA). The procedure entails first mapping the heart in order to determine where these alternative conduction pathways are located. Once these alternative conduction pathways are located, radio frequency (RF) waves are then used to create lesions in the heart which either destroys the cells that comprise these alternative conduction pathways or which blocks the conduction of electrical signals from these cells.

RFA typically involves the use of specialized ablation catheters which are designed to be inserted vascularly into a person and maneuvered into the heart. These ablation catheters carry electrodes which transmit RF waves to the tissues at an application site. The RF waves generate heat at the application site which in turn causes the cells at the application site to rupture forming a lesion in the heart tissue.

A common problem among prior art ablation catheters is the formation of coagulum around the electrodes during an RFA. As the RF waves are being delivered at the application site, both the electrode and the surrounding tissue are heated. The heat generated by the RF waves sometimes cause the electrode to overheat, causing the blood surrounding the electrode to coagulate on the electrode. The coagulum that collects on the electrode causes the impedance between the electrode and the application site to increase thereby reducing the effectiveness of the electrode to deliver the RF waves. As a result it is often necessary to stop the RFA in order to remove the coagulum from the electrode.

There are ablation catheters which currently have multiple electrodes for delivering RF energy to an application site. Many of these catheters deliver RF energy by sequentially activating the electrodes so that a linear lesion is created. The temperature of each electrode in these catheters should be monitored in order to ensure that the electrodes do not overheat and cause excess coagulum to build up. However, monitoring an electrode would typically require a temperature sensor located at the electrode and two conductive wires to relay information from the sensor. Consequently, as more electrodes are carried by the ablation catheter, more and more of the catheter's internal area is taken up by conductive wires. The amount of conductive wires which need to travel through an ablation catheter can put limitations on the size, flexibility and maneuverability of the ablation catheter.

Accordingly, it is an object of this invention to provide an ablation catheter which is capable of monitoring the temperature of its electrodes.

Accordingly, it is also an object of this invention to provide a means for measuring the temperature of a plurality of electrodes that occupy minimal space in an ablation catheter.

To achieve these objectives, and in accordance with the purposes of the present invention the following ablation catheter is presented. As will be described in greater detail hereinafter, the present invention provides the aforementioned and employs a number of novel features that render it highly advantageous over the prior art.

SUMMARY OF THE INVENTION

In accordance with an illustrative embodiment of the present invention, an ablation catheter is provided which comprises an elongated catheter body, a plurality of electrodes, and a thermal monitoring circuit. In order to minimize the number of wires needed to monitor the temperature of the electrodes, the thermal monitoring circuit is comprised of a plurality of thermocouples joined in series. The thermal monitoring circuit will require only two wires to travel through the elongated catheter body in order to monitor a plurality of electrodes. In contrast, the prior art would typically require two wires to travel to and from each electrode.

For purposes of illustration, an embodiment of the thermal monitoring circuit is presented wherein the thermocouples are connected in series with a sensing junction and a reference junction of each thermocouple thermoconductively coupled to different electrodes. Once an electrode is activated the heat from the electrode will cause the reference or sensing junction thermoconductively coupled to the activated electrode to generate a voltage from which a temperature for the activated electrode can be calculated therefrom.

Also for the purposes of illustration, an alternative embodiment of the thermal monitoring circuit is presented. This alternative embodiment has the sensing junctions thermoconductively coupled to the electrodes while the reference junctions are disposed in a central lumen in the elongated catheter body. Once again, if only one electrode is activated, the activated electrode will cause a thermocouple to generate a voltage from which the temperature of the activated electrode can be calculated therefrom.

A more detailed explanation of the invention is provided in the following description and claims, and is illustrated in the accompanying drawings.

DETAILED DESCRIPTION OF ILLUSTRATIVE EMBODIMENTS

Figure 1:
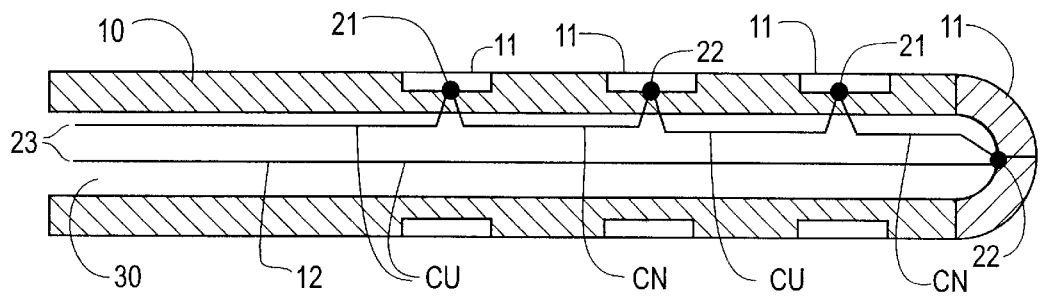
FIG. 1 is a diagrammatic side section view of the distal end of an ablation catheter embodying employing a thermal monitoring circuit in accordance with the present invention.

Referring to FIG. 1, an embodiment of the present invention is comprised of an elongated catheter body 10, a plurality of electrodes 11 carried on the distal end of the elongated catheter body, and a thermal monitoring circuit 12 comprised of a plurality of thermocouples connected in series. In order to minimize the number of wires needed to monitor the temperature of the electrode 11, the thermal monitoring circuit 12 is comprised of a plurality of thermocouples joined in series. The thermal monitoring circuit will require essentially only two wires in order to monitor a plurality of electrodes. In contrast, the prior art would typically require two wires to travel to and from each electrode.

Figure 2:
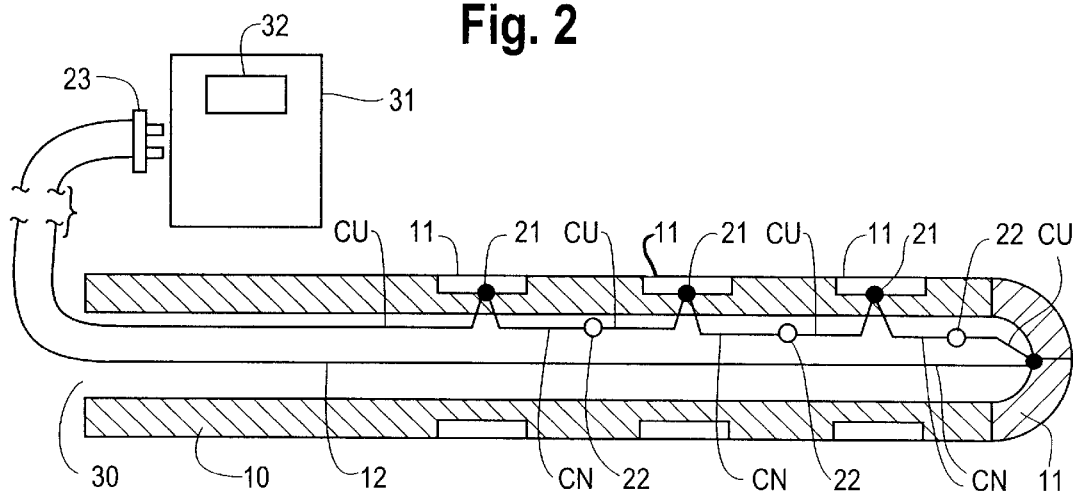
FIG. 2 is a diagrammatic side section view of the distal end of an ablation catheter with an alternate configuration for the thermal monitoring circuit.

Referring to FIG. 2, the plurality of electrodes 11 are preferably coupled to an RF generator 31 by a single RF lead (not shown). The RF generator 31 is preferably capable of delivering RF energy to each electrode independently and synchronously. The preferred RF generator 31 also has a processing means connected in circuit to the thermal monitoring circuit 12 and a visual display 32 for displaying electrode temperature. The processing means calculates the temperature from the voltages at a terminal 23. The terminal 23 is preferably connected to the processing means 31 through the use of a T-type connector, but it is understood that a variety of different connecting means can be utilized to connect the terminal 23 to the processing means 31.

Figure 3:
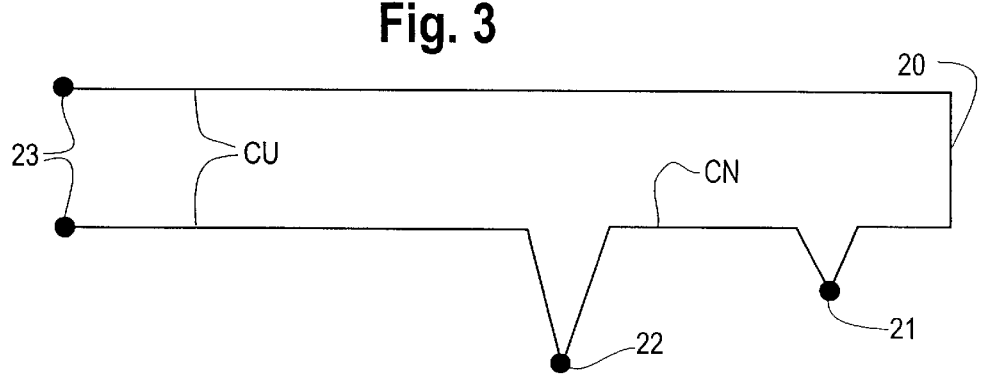
FIG. 3 is a schematic circuit diagram of a thermocouple.

For purposes of illustration, the thermocouples shown in FIGS. 1, 2, and 3 are comprised of alternating lengths of copper (CU) and constantan (CO) wire, and the wire segments comprising these materials are labeled as such. However, thermocouples can be made from a variety of metal pairs and is not necessarily limited to copper and constantan. It should be understood that thermocouples employing a metal pair other than copper and constantan can be used with the present invention.

Referring to FIG. 3, a thermocouple 20 operates on the thermoelectric principle that when two dissimilar metals are joined together, an electrical voltage is generated which is proportional to the metal composition and junction temperature (Seebeck effect). A thermocouple 20 is typically comprised of a sensing junction 21 and a reference junction 22 and a terminal 23. The reference junction 22 and the sensing junction 21 will produce DC voltages having opposite polarities and in proportion to the temperature at each junction. Consequently, if there is a difference in temperature between the sensing junction and the reference junction, a DC voltage will be produced at the terminal 23. If there is no difference in temperature between the sensing junction 21 and the reference junction 22, the voltages from the reference junction and the sensing junction will cancel each other out and there will be no voltage across the terminal 23. Referring to FIGS. 1 and 2, a plurality of thermocouples 20 connected in series will generate a voltage at the terminal 23 equal to the sum of the voltages generated by each thermocouple.

Referring to FIG. 1, in this embodiment of the thermal monitoring circuit 12, the thermocouples are connected in series with the sensing junction 21 and the reference junction 22 of each thermocouple 20 thermoconductively coupled to different electrodes 11, preferably attached thereto. Once the elongated catheter body is inserted into the body, both the reference junctions and the sensing junctions are kept at relatively the same temperature, namely body temperature. Once an electrode 11 is activated, the heat from the electrode will cause the reference 22 or sensing junction 20 thermoconductively coupled to the activated electrode to generate a voltage, either positive or negative. If only one electrode is activated, the voltage at the terminal 23 is generated by the activated electrode. The absolute value of this voltage is reflective of the temperature at the activated electrode, and a temperature for the activated electrode can be calculated therefrom.

Referring to FIG. 2, in an alternative embodiment of the thermal monitoring circuit 12 50% of the thermocouple junctions will be attached to an electrode 11 while the other 50% will be thermally isolated from the electrode 11. This can be achieved by thermoconductively coupling the sensing junctions 21 to the electrodes 11 and thermally isolating the reference junctions 22 from the electrodes 11. In this configuration, a baseline voltage will be generated at the terminal 23 due to body heat. If only one electrode 11 is activated, an additional voltage at the terminal 23 is generated by the activated electrode, and a temperature for the activated electrode can be calculated therefrom. If all the electrodes are activated in unison, an additional voltage attributable to the activated electrodes 11 is generated at the terminal 23. An average temperature for each electrode can be calculated therefrom by dividing the additional voltage by the number of electrodes and calculating the average electrode temperature therefrom.

One way of thermally isolating the reference junctions 22 from the electrodes is by disposing the reference junctions in a central lumen 30 in the elongated catheter body 10. By disposing the reference junctions in the central lumen 30, the reference junctions 22 can be placed in the path of the irrigation flow which runs through the catheter. The irrigation flow can provide a relatively stable reference temperature. The reference junctions 22 can also be thermally isolated from the electrodes 11, by thermally sealing and insulating the reference junction 22 from the catheter environment.

It can be seen that the ablation catheter which has been provided above allows for improved temperature monitoring while minimizing the space required for such monitoring. Although illustrative embodiments of the invention have been shown and described, it is not intended that the novel device be limited thereby. It is to be understood that this novel invention may be susceptible to modifications and variations that are within the scope and fair meaning of the accompanying claims and drawings.

What is claimed:

1. A catheter comprising:
   an elongated catheter body having a proximal and distal end;
   a plurality of electrodes mounted on said distal end of said catheter body; and
   a thermal monitoring circuit, said thermal monitoring a circuit comprising a plurality of thermocouples conductively connected in series, said thermocouples located at said distal end of said elongated catheter body, said thermocouples being each thermoconductively coupled to a separate electrode.

2. The catheter of claim 1 wherein said thermocouples each comprise a sensing junction thermoconductively coupled to an electrode and a reference junction which is thermally insulated from said electrode.

3. The catheter of claim 1 wherein said elongated catheter body has a central lumen extending therethrough, and wherein said thermocouples each comprise of a sensing junction thermoconductively coupled to an electrode, and a reference junction spaced from said electrode and positioned within said central lumen.

4. The catheter of claim 1 wherein said thermocouples each comprise two junctions and wherein 50% of the total junctions are thermoconductively coupled to electrodes and the other 50% of total junctions are thermally isolated.

5. The catheter of claim 1 wherein said thermocouples each comprise a sensing junction thermoconductively coupled to an electrode and a sealed and insulated reference junction.

6. The catheter in claim 1 wherein a single pair of lead wires extends from said thermal monitoring circuit to said proximal end of said elongated catheter body.

7. The catheter in claim 1 wherein each thermocouple comprises copper and constantan wires.

8. An ablation catheter comprising:

an elongated body having a proximal and distal end;

a plurality of electrodes mounted on the distal end of the catheter body, each electrode having a separate electrode circuit wire attached thereto providing a means for selectively delivering RF energy to each individual electrode; and a thermal monitoring circuit, the thermal monitoring circuit comprising a plurality of thermocouples conductively connected in series and located at said distal end of said elongated catheter body, said thermal monitoring circuit having a single pair of lead wires extending from said thermal monitoring circuit to said proximal end of said elongated catheter body, said thermocouples being each thermoconductively coupled to a separate electrode.

9. The ablation catheter of claim 8 wherein said single pair of lead wires are conductively connected to a T-type connecter.

10. The ablation catheter of claim 8 wherein a series junction from each thermocouple is thermoconductively coupled to a separate electrode.

11. The ablation catheter of claim 8 wherein said thermocouples each comprise a sensing junction thermoconductively coupled to an electrode and a reference junction which is thermally insulated from the electrode.

12. The ablation catheter of claim 8 wherein said elongated catheter body has a central lumen extending therethrough, and wherein said thermocouples each comprise a sensing junction thermoconductively coupled to an electrode, and a reference junction, spaced from said electrode and positioned within said central lumen.

13. An ablation catheter monitoring system comprising:

an ablation catheter comprising an elongated catheter body having proximal and distal ends, a plurality of electrodes mounted on the distal end of said catheter body, each electrode having separate electrode circuit wires attached thereto providing a means for selectively delivering RF energy to each individual electrode, and a heat monitoring circuit, said heat monitoring circuit comprising a plurality of thermocouples conductively connected in series and located at said distal end of said elongated catheter body, a single pair of lead wires extending from said heat monitoring circuit to said proximal end of the elongated catheter body, said thermocouples being each thermoconductively coupled to a separate electrode;

processing means for reading a voltage across said single pair of lead wires extending from said heat monitoring circuit and calculating a temperature reading therefrom; and display means for displaying said calculated temperature reading, said display means connected in a circuit to the processing means.

14. The ablation catheter monitoring system of claim 13 further comprising an RF generating means for selectively delivering RF energy to each electrode through said electrode wires.

15. The ablation catheter monitoring system of claim 13 further comprising means for synchronously delivering RF energy to each electrode.

16. The ablation catheter heat monitoring system of claim 13 wherein each thermocouple comprises a sensing junction positioned adjacent to said electrode and a reference junction which is thermally insulated from said electrode.

17. The ablation heat monitoring system of claim 13 wherein said elongated catheter body has a central lumen extending therethrough, and wherein said thermocouples each comprise sensing junctions thermoconductively coupled to said electrodes and reference junctions which are spaced from said electrodes and positioned within said lumen.

18. A method for determining the temperature of an activated electrode in an ablation catheter having a plurality of electrodes attached thereto, the method comprising:

thermoconductively coupling each electrode to a separate thermocouple connected together in series as a heat monitoring circuit;

electrically activating one of said electrodes:

measuring a voltage across said heat monitoring circuit, and calculating the temperature of said electrode from said voltage across said heat monitoring circuit.

19. The method of claim 18 wherein each thermocouple has a sensing junction and a reference junction, each sensing junction being thermoconductively coupled to different electrodes, and each reference junction being thermally insulated from said electrodes.

20. The method of claim 18 in which a plurality of said electrodes are simultaneously electrically activated and an average temperature of said electrodes is calculated.

\* \* \* \* \*